| (12) | United States Patent | (10) Patent No.: | US 8,501,170 B2 |
|---|---|---|---|
| | Rebulla et al. | (45) Date of Patent: | Aug. 6, 2013 |

(54) PLATELET FRACTION DERIVING FROM PLACENTAL BLOOD

(75) Inventors: Paolo Rebulla, Milan (IT); Lorenza Lazzari, Milan (IT); Valentina Parazzi, Milan (IT); Noemi Greppi, Milan (IT)

(73) Assignee: Fondazione IRCCS "CA' Granda—Ospedale Maggiore Policlinico", Milan (IT)

( * ) Notice: Subject to any disclaimer, the term of this patent is extended or adjusted under 35 U.S.C. 154(b) by 0 days.

(21) Appl. No.: 13/054,529

(22) PCT Filed: Jul. 14, 2009

(86) PCT No.: PCT/IB2009/006239
§ 371 (c)(1),
(2), (4) Date: Jan. 17, 2011

(87) PCT Pub. No.: WO2010/007502
PCT Pub. Date: Jan. 21, 2010

(65) Prior Publication Data
US 2011/0123503 A1    May 26, 2011

(30) Foreign Application Priority Data
Jul. 18, 2008  (IT) .............................. MI2008A1316

(51) Int. Cl.
*C12C 1/00* (2006.01)
*A01N 63/00* (2006.01)

(52) U.S. Cl.
USPC ..................................... 424/93.72; 424/93.1

(58) Field of Classification Search
USPC .............................................. 424/93.72, 93.1
See application file for complete search history.

(56) References Cited

U.S. PATENT DOCUMENTS

2003/0198687 A1*  10/2003  Bennett et al. ................. 424/532
2009/0202981 A1*  8/2009  Smith ............................... 435/2

FOREIGN PATENT DOCUMENTS

| WO | 2004076637 | 9/2004 |
| WO | 2005065269 | 7/2005 |

OTHER PUBLICATIONS

Iruloh et al. (Taurine transporter in fetal T lymphocytes and platelets: differential expression and functional activity. Am. J. Physiol Cell Physiol (2006) 292:C332-341).*
Foley, M.E. & McNicol, G.P., "An in-vitro study of acidosis, platelet function, and perinatal cerebral intraventricular haemorrhage," Lancet, vol. 1, No. 8024, Jun. 11, 1977, pp. 1230-1232.
International Search Report and Written Opinion mailed Apr. 2, 2010 in co-related pending International Application No. PCT/IB2009/006239, 14 pages.

* cited by examiner

*Primary Examiner* — Karen Cochrane Carlson
*Assistant Examiner* — Natalie Moss
(74) *Attorney, Agent, or Firm* — Meunier Carlin & Curfman, LLC

(57) ABSTRACT

The present invention relates to platelet fractions which can be obtained from placental blood, with high concentrations of platelet factors as well as gels and lysates deriving therefrom. The invention further relates to methods for preparing said platelet fractions from placental blood, and to the uses thereof as such or as platelet gels or as lysates.

14 Claims, 2 Drawing Sheets

PLATELET FRACTION DERIVING FROM PLACENTAL BLOOD

The present invention relates to platelet fractions which can be obtained from placental blood, with high concentrations of platelet factors as well as gels and lysates deriving therefrom. The invention further relates to methods for preparing said platelet fractions from placental blood and uses thereof as such or as platelet gels or as lysates.

It is known in the art that human or animal blood contains a platelet fraction. Said platelet fraction contains platelets and other factors or proteins associated thereto and can be in the form of a suspension, such as e.g. platelet plasma, or in a solid form, such as e.g. freeze-dried plasma.

In particular, the platelet fraction can be found in the lighter blood part (plasma) and can be divided into two portions, i.e. platelet-poor plasma (PPP) and platelet-rich plasma (PRP). The division can be obtained by further centrifugation.

In the context of the present invention, the term platelet-poor plasma (PPP) refers to the lighter plasma portion and includes platelets in a concentration below one million per microliter.

In the context of the present invention, the term platelet-rich plasma (PRP) refers to the less light plasma portion and includes platelets in a concentration above one million per microliter.

The platelet fraction, preferably the PRP portion, is known in the art as being useful both in vivo and in vitro.

The platelet fraction can be used in vivo as a hemostatic agent. By using said platelet fraction as a hemostatic agent when platelets are lysated, a therapeutic and stimulating effect could also be observed on surgery-related lesions. This further resulted in a second in-vivo application, i.e. the preparation of medicaments for treating lesions, and injuries or for increasing the re-growth of a variety of damaged tissues.

The platelet fraction can also be used in vitro as part of a cell culture medium for keeping in-vitro cell cultures vital and/or for stimulating the growth of in-vitro cell cultures. Said culture medium is known in the art and is used in expansion or maintenance protocols for cell cultures, among which stem cells (e.g. mesenchymal stem cells or hematopoietic stem cells). Said medium can include the platelet fraction, preferably lysated, both in the form of a solution or as a gel, which is mixed with the cells during cell culture.

Sources of platelet fractions that are known in the art are mammal blood, in particular human blood. For the use as a culture medium, a platelet fraction deriving from bovine blood serum is used. For in-vivo uses, the platelet fraction derives from human peripheral blood.

Said sources of platelet components involve quite relevant drawbacks and problems.

Peripheral blood from a human (allogeneic blood, of non-autologous origin but from a subject belonging to the same species) cannot be used since the immune system of a human does not recognize said platelet fraction as autologous and said recognition results in various medical and clinical complications that are well known in the art as far as methods and devices for transplants are concerned.

The availability of autologous blood is generally low since it can be dangerous to withdraw a sufficient amount from a patient who cannot tolerate such a withdrawal, e.g. due to old age, weakness, clinical and medical complications associated to said withdrawal.

Allogeneic blood can involve risks of infections and as is well known, compatible allogeneic blood is hard to find.

The use of the platelet fraction deriving from bovine or calf blood serum is limited to in-vitro applications which do not enable uses for treatments or interactions with the human body for obvious health reasons related to the possible transmission of animal infections or contaminations from animal biological tissues.

Therefore, there is still the problem of finding a platelet fraction which can overcome the problems disclosed above, keeping and even increasing its application potential.

The Applicant has surprisingly found that platelet fractions deriving from human placental blood can meet the needs referred to above and are more effective for the same uses.

In the context of the present invention, the term placental blood refers to blood taken from the placenta, preferably from the umbilical cord.

An object of the present invention is a platelet fraction which can be obtained from mammal placental blood. Preferably, the mammal placental blood is human placental blood.

Said platelet fraction can be obtained from placental blood by a method suitably chosen by the skilled technician among those that are already known in the art. Preferably, the method includes the following steps:

i) preparing placental blood, and
ii) isolating the placental fraction from moieties present in blood and heavier than the platelet fraction.

Preferably, this isolation occurs by centrifugation, wherein the platelet fraction is isolated as the lighter component resulting from centrifugation.

In a preferred embodiment, a sample of placental blood is prepared in 1-50 ml aliquots, preferably 15-40 ml, more preferably 25-35 ml, and centrifugation is carried out at a rotation in the range of 300 to 900 g, preferably of 450 to 700 g, more preferably of 500 to 600 g, for a period in the range of 5 to 20 minutes, preferably of 7 to 15 minutes, more preferably of 9 to 11 minutes.

Preferably, at least one subsequent centrifugation is carried out at a rotation in the range of 50 to 200 g, preferably of 70 to 150 g, more preferably of 90 to 110 g, for a period of 5 to 15 minutes, preferably of 7 to 13 minutes, more preferably of 9 to 11 minutes, for removing any lymphocytes present, so as to prevent a resulting platelet fraction from causing an immunogenic reaction. The value of lymphocytes that may be present is preferably below $5 \times 10^3$ lymphocytes/ml, more preferably below $1 \times 10^3$ lymphocytes/ml. The presence of lymphocytes can be determined by using an automatic hemocytometer such as e.g. ABX Micros CRP.

Said platelet fraction is characterized by a higher concentration of platelet factors than human peripheral blood. Preferably, said platelet factors include a selection of growth factors, hormones and cytokines. In particular, the concentration of said platelet factors is higher for angiogenesis-directed platelet factors. Said angiogenesis-directed platelet factors are preferably soluble factors and include more preferably the following growth factors:

FGFB (Basic fibroblast growth factor),
PDGF (Platelet-derived growth factor) isoform BB,
TGF-beta (Transforming growth factor, beta sub-species) and
VEGF (Vascular endothelial growth factor).

The concentration of platelet factors in the platelet fraction can be quantified by methods known in the art and suitably chosen by the skilled technician, more preferably by protocols making use of ELISA technology (Enzyme-Linked ImmunoSorbent Assay).

In the context of the present invention, the platelet fraction can be divided into a PPP portion and PRP portion. PPP and PRP portions can be prepared starting from the platelet fraction according to the invention by a subsequent centrifugation of the platelet fraction, in which the heavier component lies on the bottom in the form of a pellet. Said heavier portion is PRP and can be re-suspended in a suitable volume of physiological liquid, preferably human plasma, more preferably placental blood plasma. Said plasma can consist of a portion of plasma deriving from the centrifugation as a supernatant, i.e. of PPP itself.

The centrifugation is carried out at a rotation in the range of 1,500 to 2,500 g, preferably of 1,700 to 2,300 g, more preferably of 1,900 to 2,100 g, for a period in the range of 10 to 20 minutes, preferably of 13 to 17 minutes, more preferably of 14 to 16 minutes. Embodiments of the present invention are therefore the separate PPP and PRP portions which can be obtained from the platelet fraction according to the invention. The platelet fraction according to the invention has low immunogenicity levels, which are extremely lower than platelet fractions from allogeneic blood. The platelet fraction according to the invention further has a low level of infective contaminations, such as e.g. bacteria or viruses.

The platelet fraction according to the invention can be in liquid form, in solid form (also as a gel) or in freeze-dried form and can be stored in any device known in the art for storing platelet fractions or plasma. The platelet fractions according to the invention can be preserved by methods suitably chosen among those known in the art, such as e.g. freezing the platelet fraction at −80° C. when in a suitable volume physiologically acceptable solution, preferably plasma, more preferably placental blood plasma.

The platelet fraction according to the invention is preferably in freeze-dried form. Said freeze-dried form can be easily transported, packaged and stored.

In an embodiment of the invention, said platelet fraction is present in a pharmaceutical composition. Said pharmaceutical composition can contain excipients and, depending on the needs and on the desired specific formulations, can contain other active substances such as e.g. other hemostatic agents or molecules for preparing specific formulations, such as e.g. demulcents and surfactants.

Another object of the present invention is a method for preparing a platelet fraction as already described above.

A further object of the invention are the products deriving from the lysis and/or activation of the platelet fraction which can be obtained as described above, preferably from PRP platelet fraction. Said derived products are preferably the lysated and/or activated platelet fraction and include the same platelet factors as mentioned above, but are separated from platelet macromolecular structures and can therefore be accessed and used more easily.

The skilled technician can suitably choose among known methods and devices for carrying out said lyses and/or said activation of platelets, such as e.g. the use of collagen or thrombinic agents (such as e.g. batroxobin) in the activation of platelets in the platelet fraction.

In a more preferred embodiment, platelet activation produces a platelet gel. The skilled technician can suitably choose among methods known in the art for preparing platelet gels. Preferably, the platelet fraction to be activated is in liquid form or is converted into liquid form, such as e.g. by re-suspension in a suitable volume of physiological solution, before being activated.

The activation of the platelet fraction preferably includes the steps of adding and mixing 0.1 to 2 ml, preferably 0.5 to 1.5 ml, more preferably 0.9 to 1.1 ml of calcium gluconate and 0.1 to 2 NIH thrombinic units, preferably 0.5 to 1.5 NIH thrombinic units, more preferably 0.8 to 1 thrombinic unit of batroxobin per 5-6 ml, preferably 5.5 ml of the platelet fraction.

0.9 NIH thrombinic units of batroxobin are preferably construed as corresponding to about 5 Bethesda units. Preferably, batroxobin is freeze-dried.

In a preferred embodiment, after platelet activation the mixture is left to rest so that it forms a gel. Preferably, the mixture is left to rest for at least 2 minutes, more preferably for at least 5 minutes, still more preferably for at least 8 minutes and even more preferably for at least 10 minutes.

The lysate can be obtained by a method including a step of lysis of the platelet fraction according to the invention. The lysis of the platelets in the platelet fraction, preferably PRP, can be carried out so as to obtain a suspension of platelet factors. The lysis is performed by methods known in the art, such as application of sudden heat variations, use of surfactants or, preferably, use of a centrifuge at a rotation of at least 1,700 g, preferably at a rotation in the range of 1,700 to 2,500 g, preferably of 1,800 to 2,300 g, more preferably of 1,900 to 2,150 g, for a period in the range of 5 to 20 minutes, preferably of 7 to 15 minutes, more preferably of 9.5 to 10.5 minutes. In an embodiment the lysis can be performed on platelet fractions that have already been activated, e.g. on a platelet gel.

The product obtained from the lysis is preferably freeze-dried according to methods and with devices known in the art so as to obtain a freeze-dried lysate in powder form.

The lysate obtained as described above can be adsorbed on biocompatible matrices. Said biocompatible matrices can be made of synthetically obtained material, such as e.g. retronectin or ceramics such as e.g. hydroxyapatite, or biological material, such as e.g. collagen. Still more preferably, the biocompatible matrix is part of a plaster or bandage. More preferably, the matrix containing the platelet lysate is located so as to be contacted with the injury when the plaster or bandage is applied thereon.

Another object of the invention is a bioreactor comprising a platelet fraction or products deriving therefrom as described above. Said bioreactor is any device which is able to allow the in-vitro expansion or maturation of cellular material capable of reproducing itself by cell expansion or maturation. Preferably, said cellular material capable of reproducing itself is made up of eukaryotic cells, more preferably from human, still more preferably stem cells or precursors known in the art for their potential of numeric expansion. Preferably, said bioreactor is a Petri dish or a cell culture bag, wherein the cellular material capable of reproducing itself is mixed with the platelet fractions or the products deriving therefrom as described above.

The platelet fraction, or the products deriving therefrom as described above, is advantageous since it allows a greater cell expansion and differentiation in a bioreactor and at the same time keeps the same potential or multipotential of the same mother cells. Preferably, the cells in the bioreactor are stem cells, preferably mesenchymal cells.

Another aspect of the invention is the use of the platelet fractions, or of the products deriving therefrom, as a medicament. Preferably, the products deriving therefrom are lysates and/or a component obtained from the activation of the platelet fraction.

In a preferred embodiment, the platelet fractions, or the products deriving therefrom, are used as a medicament, or alternatively in the preparation of said medicament, for treating, stopping and/or preventing accidental blood losses such as hemorrhages. In said embodiment, the medicament can advantageously contain excipients and/or other hemostatic agents.

In another preferred embodiment, the platelet fractions, or the products deriving therefrom, are used as a medicament, or alternatively in the preparation of said medicament, for the re-growth or treatment of any damaged animal tissue. In the context of the present invention, a damaged tissue is defined as a tissue requiring a re-growth due to a disease or an injury caused e.g. by a foreign body. Preferably, said damaged animal tissue is an injury and/or a lesion on animal muscular or cutaneous tissue. Preferably, re-growth means cicatrisation, vascularisation or healing of an injury or lesion. Still more preferably, the injury and/or lesion is due to a cutaneous ulcer.

In said embodiment, the platelet fraction is preferably in the form of a lysate or in the form of a platelet gel as described above.

In another embodiment of the invention, the platelet fraction is used in in-vitro expansion or maturation of cellular biological material capable of reproducing itself, preferably in a bioreactor, as already described above.

The present invention is disclosed in the following detailed description and further exemplified below thanks to the accompanying figures.

EXAMPLE 1

Figure 1:
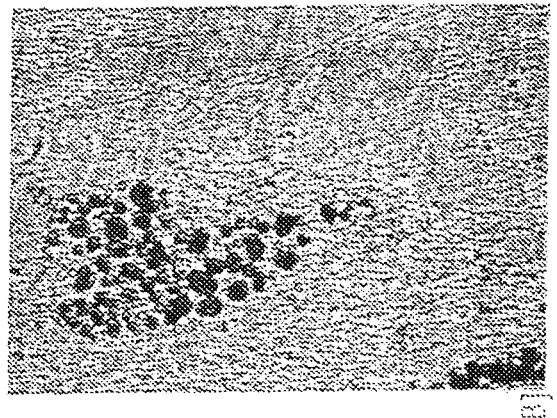
FIG. 1 shows the comparison in the growth of mesenchymal stem cells for three weeks (see Example 3), then subjected to adipogenic differentiation (see Example 4), when as a culture DMEM and 10% v/v of platelet lysate obtained from placental blood (FIG. 1A) are used, and when as a culture DMEM and 10% v/v of platelet lysate obtained from peripheral blood (FIG. 1B) are used.
Figure 1:
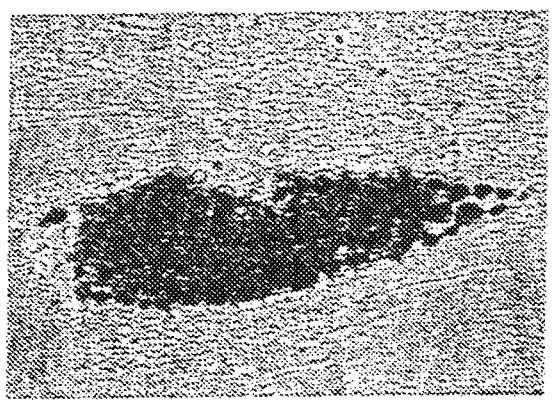

Preparation of Platelet Fraction and then of PRP from Placental Blood

An hemochrome was performed with a hemocytometer ABX Micros CRP on a bag of placental blood from the Cord Blood Bank of Milano, in order to known platelet concentration.

Blood was then transferred into 50 ml tubes in 25-30 ml aliquots and then centrifuged at 550 g for 10 minutes.

The plasma portion, containing the platelet fraction and located above the lymphocyte ring, was withdrawn with a pipette.

Then said portion was centrifuged at 2,000 g for 15 minutes.

The resulting pellet was re-suspended in 5.5 ml of said plasma portion so as to obtain a final concentration of $2\times10^9$ plt/ml.

The result PRP sample was then left to rest at room temperature for 30 minutes.

EXAMPLE 2

Preparation of Platelet Gel from the Platelet Fraction

The protocol of Example 1 was repeated so as to obtain a 5.5 ml sample of PRP platelet fraction from placental blood having a concentration of $2\times10^9$ plt/ml.

Said sample was activated by adding 1 ml of calcium gluconate and a tablet of freeze-dried batroxobin corresponding to 5 Bethesda units and about 0.9 NIH thrombinic units.

It was waited for 10 minutes so as to obtain a platelet gel.

EXAMPLE 3

Comparison of the Effectiveness of a Culture for Cell Expansion Comprising a Platelet Fraction from Placental Blood and One Comprising a Fraction from Peripheral Blood The platelet gel prepared according to Example 2 was centrifuged at 2,000 g for 10 minutes and the supernatant was filtered with a filter having 20 micrometer pores so as to obtain a platelet lysate. A corresponding platelet lysate from peripheral blood was further prepared in the same way.

$2\times10^5$ mesenchymal stem cells were isolated from fatty tissue of human adults (with informed consent). Said mesenchymal stem cells were plated in a culture of (Dulbecco's Modified Eagle's Medium) and 10% v/v of platelet lysate obtained from placental blood and 1% v/v of penicillin/streptomycin. A culture comprising 10% v/v of lysate deriving from peripheral blood was prepared in the same way. The cells were maintained in culture for three weeks, replacing half of the culture medium once a week.

After three weeks the cells were characterized by cytofluorimetric analysis with the device cytomics C500 and the software CXP of Beckam Coulter.

Mesenchymal stem cells obtained after 3 weeks were plated in DMEM+20% v/v of FBS (fetal bovine serum) at $2.1\times10^4$ cells/cm$^2$ and incubated at 37° C. with 5% v/v of $CO_2$.

Once they have reached confluence, the cells are stimulated with three differentiation cycles. Each cycle consists in cultivating the cells obtained on said culture mediums with Adipogenesis Induction Medium (Lonza) for three days, followed by 1-3 days of culture in Adipogenic Maintenance Medium (Lonza).

After three complete cycles, the cells are maintained in culture with Adipogenic Maintenance Medium for seven days, replacing the medium every 2-3 days.

Eventually, in order to observe the actual differentiation the cells are washed with PBS, fixed in 10% v/v of formaldehyde for 10 minutes and colored with Oil Red O for 5 minutes.

Only lipid vacuoles are colored. The results can be visually compared in FIG. 1, wherein FIG. 1A shows the growth with the platelet fraction according to the invention and FIG. 1B shows the growth with the platelet fraction from peripheral blood.

Beyond the test with adipogenic differentiation, the difference in effectiveness of the platelet fraction was also measured with osteogenic differentiation.

Mesenchymal stem cells obtained from the cultures after 3 weeks, as above, were plated in a concentration of $2.1\times10^4$ cells/cm$^2$ in DMEM+20% v/v of FBS (fetal bovine serum) and incubated at 37° C. with 5% v/v of $CO_2$.

After 24 hours the culture medium was replaced with Osteogenesis Induction Medium (Lonza). The cells are maintained in culture for 3 weeks replacing the medium with fresh medium every 2-3 days.

Eventually, in order to observe the actual differentiation the cells are washed with PBS and fixed with 70% v/v of ethyl alcohol (stored at −20° C.) for 1 hour and colored with Alizarin Red S 40 mM (pH=4.1).

Figure 2:
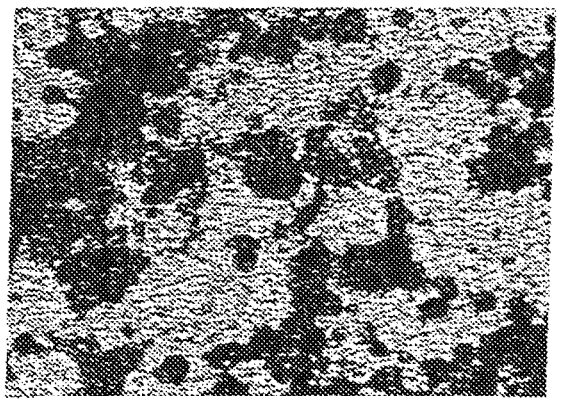
FIG. 2 shows the comparison in the growth of mesenchymal stem cells for three weeks (see Example 3), then subjected to osteogenic differentiation (see Example 4), when as a culture DMEM and 10% v/v of platelet lysate obtained from placental blood (FIG. 2A) are used, and when as a culture DMEM and 10% v/v of platelet lysate obtained from peripheral blood (FIG. 2B) are used.
Figure 2:
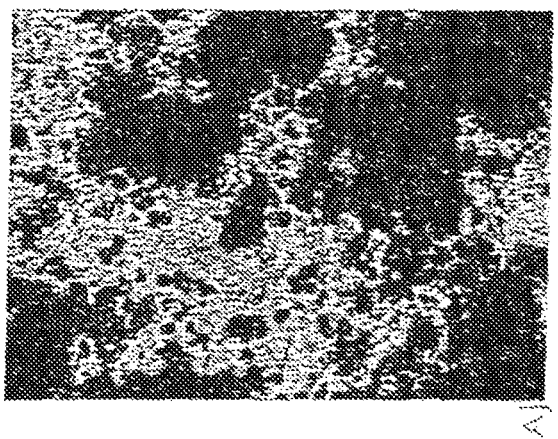

Only calcium deposits are colored. The results can be visually compared in FIG. 2, wherein FIG. 2A shows the growth with the platelet fraction according to the invention and FIG. 2B shows the growth with the platelet fraction from peripheral blood.

The comparison for both types of differentiation shows that the use of the platelet fraction deriving from placental blood has an evident effect on the potential of said mesenchymal stem cells.

In particular it was observed that, beyond supporting the growth and expansion of stem cells, the platelet fraction from placental blood maintains the multipotential thereof, i.e. the capacity of giving rise to different tissues of other origin: in this specific case of a mesenchymal stem cell giving rise, according to experimental protocols, to a fatty tissue or to an osteogenic tissue.

The advantageous properties of the placental platelet lysate for use in a culture for cell expansion are further confirmed by the cytofluorimetric analysis of stem markers detected as present or not present on mesenchymal stem cells obtained after a 3-week growth on cultures comprising a platelet fraction from placental blood compared with mesenchymal stem cells obtained after a 3-week growth on cultures comprising a platelet fraction from peripheral blood.

The invention claimed is:

1. A method for preparing a platelet fraction, said method comprising the following steps:
    (i) preparing a placental blood sample,
    (ii) centrifuging the placental blood sample at a rotation comprising between 300 to 900 g for a period that varies from 5 to 20 minutes; and
    (iii) centrifuging the placental blood sample at a rotation comprising between 50 to 200 g for a period that varies from 5 to 15 minutes.

2. The method according to claim 1 further comprising a centrifuging step carried out at a rotation comprising between 1,500 to 2,500 g for a period that varies from 10 to 20 minutes.

3. The method according to claim 1 further comprising an activation step of the platelet fraction.

4. The method according to claim 2 further comprising an activation step of the platelet fraction.

5. The method according to claim 3, wherein said activation step comprises adding and mixing from 0.1 to 2 ml of calcium gluconate and from 0.1 to 2 NIH thrombinic units of batroxobin per 5.5 ml of the platelet fraction.

6. The method according to claim 4, wherein said activation step comprises adding and mixing from 0.1 to 2 ml of calcium gluconate and from 0.1 to 2 NIH thrombinic units of batroxobin per 5.5 ml of the platelet fraction.

7. The method according to claim 3 further comprising a step of lysis of the platelet fraction by centrifuging at a rotation of at least 1,700 g, for a period in the range of 5 to 20 minutes.

8. The method according to claim 7, wherein the centrifugation is performed at a rotation comprising between 1,700 to 2,500 g.

9. The method according to claim 7, wherein the platelet fraction is PRP.

10. The method according to claim 8, wherein the platelet fraction is PRP.

11. The method according to claim 1, wherein said platelet fraction contains less than $5 \times 10^3$ lymphocytes/$2 \times 10^9$ platelets.

12. The method according to claim 1, wherein said platelet fraction contains less than $1 \times 10^3$ lymphocytes/$2 \times 10^9$ platelets.

13. The method according to claim 1, wherein said platelet fraction is on a biocompatible matrix.

14. The method according to claim 13, wherein said matrix is a plaster or a bandage.

* * * * *